(12) United States Patent
Placik et al.

(10) Patent No.: US 9,414,941 B2
(45) Date of Patent: Aug. 16, 2016

(54) SYSTEM AND METHOD FOR INSERTING A PLIABLE IMPLANT THROUGH A SURGICAL INCISION USING A MULTI-STAGE COMPRESSION SLEEVE

(71) Applicants: Otto J. Placik, Arlington Heights, IL (US); Jay Pensler, Chicago, IL (US)

(72) Inventors: Otto J. Placik, Arlington Heights, IL (US); Jay Pensler, Chicago, IL (US)

( * ) Notice: Subject to any disclaimer, the term of this patent is extended or adjusted under 35 U.S.C. 154(b) by 0 days.

(21) Appl. No.: 14/536,544

(22) Filed: Nov. 7, 2014

(65) Prior Publication Data

US 2015/0297339 A1  Oct. 22, 2015

Related U.S. Application Data

(60) Provisional application No. 61/954,555, filed on Mar. 17, 2014.

(51) Int. Cl.
| | | |
|---|---|---|
| *A61F 2/12* | (2006.01) | |
| *A61F 2/52* | (2006.01) | |
| *A61F 2/00* | (2006.01) | |
| A61B 17/00 | (2006.01) | |
| A61B 18/00 | (2006.01) | |

(52) U.S. Cl.
CPC ............... *A61F 2/52* (2013.01); *A61F 2/0095* (2013.01); *A61F 2/12* (2013.01); *A61B 2017/00796* (2013.01); *A61B 2018/00333* (2013.01); *A61F 2230/0063* (2013.01); *A61F 2230/0069* (2013.01)

(58) Field of Classification Search
CPC ............. A61F 2/52; A61F 2/12; A61F 19/24; A61F 2017/00796; A61F 2018/00333; A61F 2/962; A61F 2/97; A61F 2/07
See application file for complete search history.

(56) References Cited

U.S. PATENT DOCUMENTS

| | | | | |
|---|---|---|---|---|
| 4,143,428 A | * | 3/1979 | Cohen | A61F 2/12 604/407 |
| 4,341,211 A | * | 7/1982 | Kline | A61M 31/007 604/514 |
| 4,955,906 A | * | 9/1990 | Coggins | A61F 2/12 623/8 |
| 5,201,779 A | * | 4/1993 | Shiao | A61B 17/3468 604/59 |
| 5,630,843 A | * | 5/1997 | Rosenberg | 604/288.01 |
| 6,383,191 B1 | * | 5/2002 | Zdeblick | A61B 17/3421 606/105 |
| 7,146,984 B2 | * | 12/2006 | Stack | A61F 2/04 128/898 |
| 8,550,090 B2 | | 10/2013 | Keller et al. | |
| 8,641,758 B1 | * | 2/2014 | Anderson | A61B 17/0206 623/23.64 |
| 2003/0130611 A1 | * | 7/2003 | Martin | A61F 2/07 604/8 |
| 2005/0085923 A1 | * | 4/2005 | Levine | A61F 17/0401 623/23.65 |
| 2005/0192668 A1 | * | 9/2005 | Studin | A61F 2/12 623/8 |

(Continued)

*Primary Examiner* — Christian Sevilla
*Assistant Examiner* — Seema Mathew
(74) *Attorney, Agent, or Firm* — LaMorte & Associates, P.C.

(57) ABSTRACT

A system and method for advancing an implant into a surgical incision. The implant is placed into a compression sleeve. The compression sleeve has a first open end, a second open end, a first stage of a first length, and a second stage of a second length. The cross-sectional profile of the first stage is larger than the cross-sectional profile of the second stage. The implant is inserted into the first stage of the compression sleeve through the open first end. The compression sleeve is compressed to advance the pliable prosthetic implant at least partially into the second stage of the compression sleeve. The open second end of the compression sleeve is directed into a surgical incision. The compression sleeve is further compressed to advance the pliable prosthetic implant through the second stage, through the open second end, and into the surgical incision.

16 Claims, 6 Drawing Sheets

(56) References Cited

U.S. PATENT DOCUMENTS

| | | | |
|---|---|---|---|
| 2009/0177165 A1* | 7/2009 | Tsao | A61F 2/12 604/181 |
| 2009/0204107 A1 | 8/2009 | Keller et al. | |
| 2010/0280610 A1* | 11/2010 | Preissman | A61F 2/12 623/8 |
| 2011/0035003 A1 | 2/2011 | Preissman | |
| 2011/0264234 A1* | 10/2011 | Baker | A61F 2/04 623/23.64 |
| 2014/0228951 A1* | 8/2014 | Zochowski | A61F 2/12 623/8 |
| 2015/0032208 A1* | 1/2015 | Preissman | A61F 2/12 623/8 |
| 2015/0126812 A1* | 5/2015 | Anderson | A61B 17/02 600/203 |

* cited by examiner

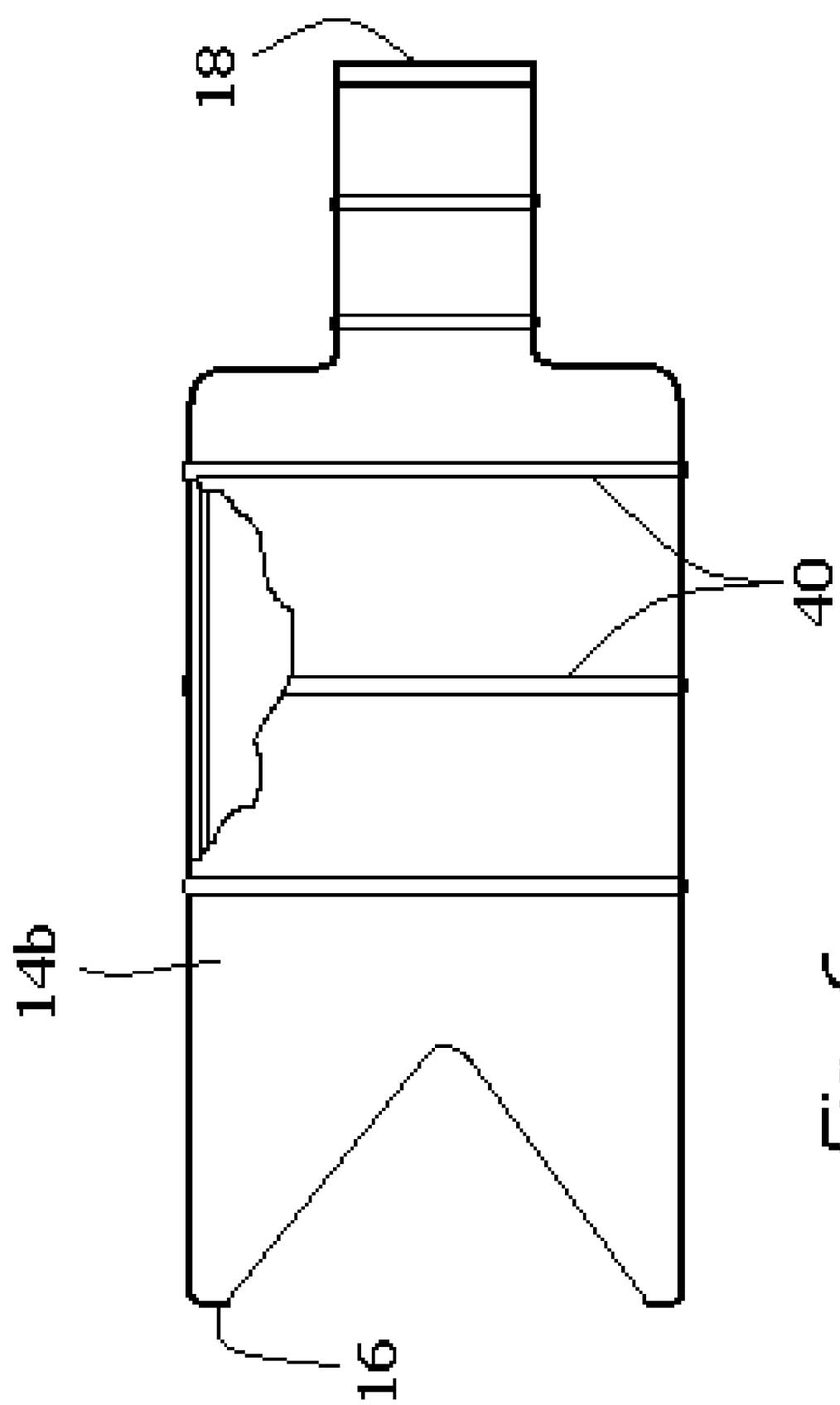

SYSTEM AND METHOD FOR INSERTING A PLIABLE IMPLANT THROUGH A SURGICAL INCISION USING A MULTI-STAGE COMPRESSION SLEEVE

RELATED APPLICATIONS

This application claims benefit of U.S. Patent Provisional Application No. 61/954,555 filed Mar. 17, 2014.

BACKGROUND OF THE INVENTION

1. Field of the Invention

In general, the present invention relates to devices and methods for compressing and insertion of a pliable prosthetic implant, such as a breast augmentation implant, and advancing the prosthetic implant through a small diameter incision during a surgical procedure in a manner to reduce the risk of infection.

2. Prior Art Description

Breast augmentation surgery that utilizes breast implants has been widely practiced by surgeons for decades. In this period or time, the implants, techniques, and instruments used during the surgery have continued to evolve. The results are patients that required less time under anesthetic, patents having smaller incisions, improved feel of the implant simulating indigenous tissue and patients having more natural appearing and results.

In a modern breast augmentation procedure, a small incision is made in or near the breast. A breast implant is then deformed through the small incision and into the surgical pocket beneath the breast tissue. This is typically accomplished by the surgeon manipulating the implant through the incision in direct contact with the patient's tissue or placement via an insertion instrument, such as a sleeve as originally described by Mladick in "Twelve Months of Experience with Bioplastique", Aesth. Plast. Surg., 16: 69-76, 1992, or a modification of the sleeve such as a funnel as described by Keller and others (patents cited below). Such funnels are little more than conical tubes, such as those used for cake decorating. The implant is placed into the large end of the funnel. The small end of the funnel is then placed in the incision. The implant is forced through the funnel and into the incision by continually squeezing and compressing the funnel. Such prior art funnel systems are exemplified by U.S. Patent Application Publication No. 2009/0204107, entitled "Apparatus and Process for Delivering a Silicone Prosthesis into a Surgical Pocket"; U.S. Patent Application Publication No. 2010/0280610, entitled "Silicone Breast Implant Delivery;" U.S. Patent Application Publication No. 2011/0035003, entitled "Fail-safe Silicone Breast Implant Delivery Device"; and U.S. Pat. No. 8,550,090 to Keller, entitled Apparatus And Process For Delivering A Silicone Prosthesis into A Surgical Pocket.

U.S. Pat. No. 8,641,758 to Anderson, entitled Method And Apparatus For Inserting A Filled Prosthetic Bladder Into A Patient, discloses a funnel shaped instrument that deforms a pliable prosthetic implant into a small incision. However, due to the funnel shape, the device has the same disadvantages as prior art funnel-shaped compression bags.

The use of prior art funnels, sleeves, or other systems has both advantages and disadvantages. The advantages of a prior art funnel, sleeve, or other system include the fact that the use of the funnel, sleeve, or other system only requires a small incision to be made in the breast. Furthermore, when an implant is used, the implant only touches the sterile interior of the funnel, sleeve, or other system as it is being advanced into the body. This "no-touch" system minimizes contamination issues and the occurrence of capsular contracture due to contamination.

The specific disadvantages of using a funnel include the fact that the implant is forced into a conical shape as it conforms to the interior of the funnel. This conical shape is analogous to the shape of a cork stopper in a bottle. This conical shape is then physically forced though the small exit diameter of the funnel. A large amount of force is required to advance the implant in the funnel. This force is applied manually by the surgeon. To achieve the needed force, the surgeon must often wind and crumple the funnel. This can damage the implant, particularly the shell, if the implant gets caught in a fold of the crumple. The build-up of forces can also cause permanent bulges in the shell of the implant, which adversely affects the aesthetics of the implant. Furthermore, the force applied by the surgeon builds until the implant suddenly ejects from the funnel and into the tissue of the breast at an uncontrolled rate which is a particularly difficult to monitor due to the opaque nature of the funnel. This makes it nearly impossible to visualize damage or proper orientation of the implant as it is ejected from the funnel or other sleeve like devices. This can cause unnecessary bruising and tearing of tissue both inside the breast and at the incision. If proper orientation of the implant cannot be achieved by happenstance as it is ejected from the device, the surgeon must typically manipulate the implant thereby negating the "no touch" technique. The potential for microbial contamination is thus increased.

A need therefore exists for an improved system that can be used during a breast augmentation procedure, wherein the benefits of prior art funnel, sleeve, or other systems are maintained, but many of the disadvantages associated with funnels are eliminated or minimized. This need is met by the present invention as described and claimed below.

SUMMARY OF THE INVENTION

The present invention is a system and method for advancing a pliable prosthetic implant into a surgical incision. The pliable prosthetic implant is placed into a contiguous series of variable width non-tapering compression sleeves. The sleeve introducer system has a first open end, a second open end, a first stage of a first length, and a second stage of a second length. The first stage has a first cross-sectional profile that evenly extends along its first length. Likewise, the second stage has a second cross-sectional profile that extends along its second length. The cross-sectional profile of the first stage is larger than the cross-sectional profile of the second stage. The second length of the second stage is variable in length. Both segments of the sleeve are not tapered.

The compression sleeve is comprised of a flexible and transparent material. The pliable prosthetic implant is inserted into the first stage of the compression sleeve through the open first end. The compression sleeve is compressed to advance the pliable prosthetic implant at least partially into the second stage of the compression sleeve. The open second end of the compression sleeve is directed into a surgical incision. The compression sleeve is further compressed to advance the pliable prosthetic implant through the second stage, through the open second end, and through the surgical incision into the dissected pocket for the implant.

BRIEF DESCRIPTION OF THE DRAWINGS

For a better understanding of the present invention, reference is made to the following description of exemplary embodiments thereof, considered in conjunction with the accompanying drawings, in which:

FIG. 6 shows the compression sleeve supplemented with ribs.

DETAILED DESCRIPTION OF THE DRAWINGS

Although the present invention system can be embodied in different ways to facilitate different sized and types of pliable prosthetic implants, only some exemplary embodiments are illustrated and described. These embodiments are selected in order to set forth the best modes contemplated for the invention. The illustrated embodiments, however, are merely exemplary and should not be considered a limitation when interpreting the scope of the appended claims.

Figure 1:
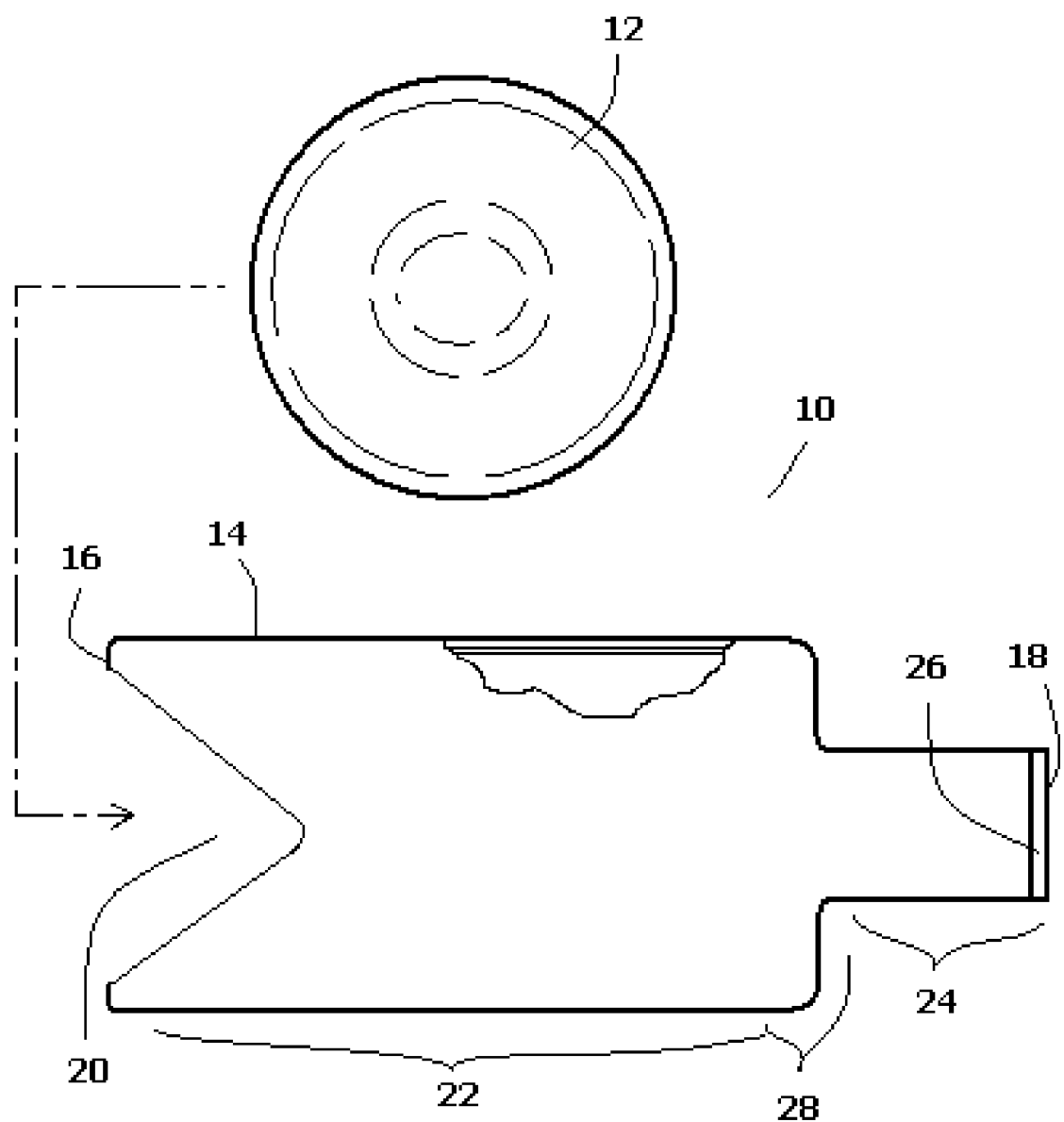
FIG. 1 is front view of a system showing a compression sleeve and a breast implant.

Referring to FIG. 1, a system 10 is shown that can be used to advance a large diameter pliable prosthetic implant 12 through a small diameter incision during a surgical procedure. The system 10 utilizes a compression sleeve 14. The compression sleeve 14 has an open first end 16 and an open second end 18. The open first end 16 may contain side slots 20 to assist in the stretching of the open first end 16 around the pliable prosthetic implant 12. The compression sleeve 14, when not stretched, contains multiple stages 22, 24. Each stage 22, 24 has a different diameter or oblong axis, depending upon its cross-sectional shape. The first stage 22 near the first open end 16 is the stage with the largest cross-sectional profile. Conversely, the last stage 24, near the second open end 18 is the stage with the smallest cross-sectional profile. In the exemplary embodiment, the compression sleeve 14 is shown with only two stages 22, 24. This is the simplest form of the invention and is used for descriptive purposes. It should be understood that more than two stages can be used in the compression sleeve 14, provided the diameter or oblong axis of each stage gets smaller as it approaches the open second end 18.

Each of the stages 22, 24 may have a round cross-sectional profile, or an oval cross-sectional profile, depending upon its method of manufacture. Round cross-sectional profiles are preferred, should the compression sleeve 14 be dip molded or vacuum molded. Oblong cross-sectional profiles can be used if the compression sleeve 14 is made by joining two sections of plastic material along a common seam in the manner of a fluid IV bag.

The unstretched diameter or long oblong axis of the last stage 24 is sized to fit into the incision made by a physician to insert a pliable prosthetic implant 12 into a patient's body. For a breast implant, such incisions are typically between three centimeters and seven centimeters in length depending upon the size and type of implant to be inserted. Compression sleeves 14 will be made in different sizes to accommodate different incision lengths and implant shapes and sizes.

The compression sleeve 14 is manufactured from a medical grade flexible plastic material, such as PVC that is mixed with a DEHP plasticizer. If the use of DEHP is undesired, alternate materials can be used, such as ethylene vinyl acetate or a polyolefin, such as polypropylene. Such materials are flexible, strong and are capable of slightly stretching without rupture. It is also preferred that the material of the compression sleeve be transparent or highly translucent. In this manner, the orientation of the pliable prosthetic implant 12 can be directly observed as it is being implanted. This provided the surgeon with the option of turning the compression sleeve 14 to keep the pliable breast implant 12 properly oriented as it enters the body.

Figure 2:
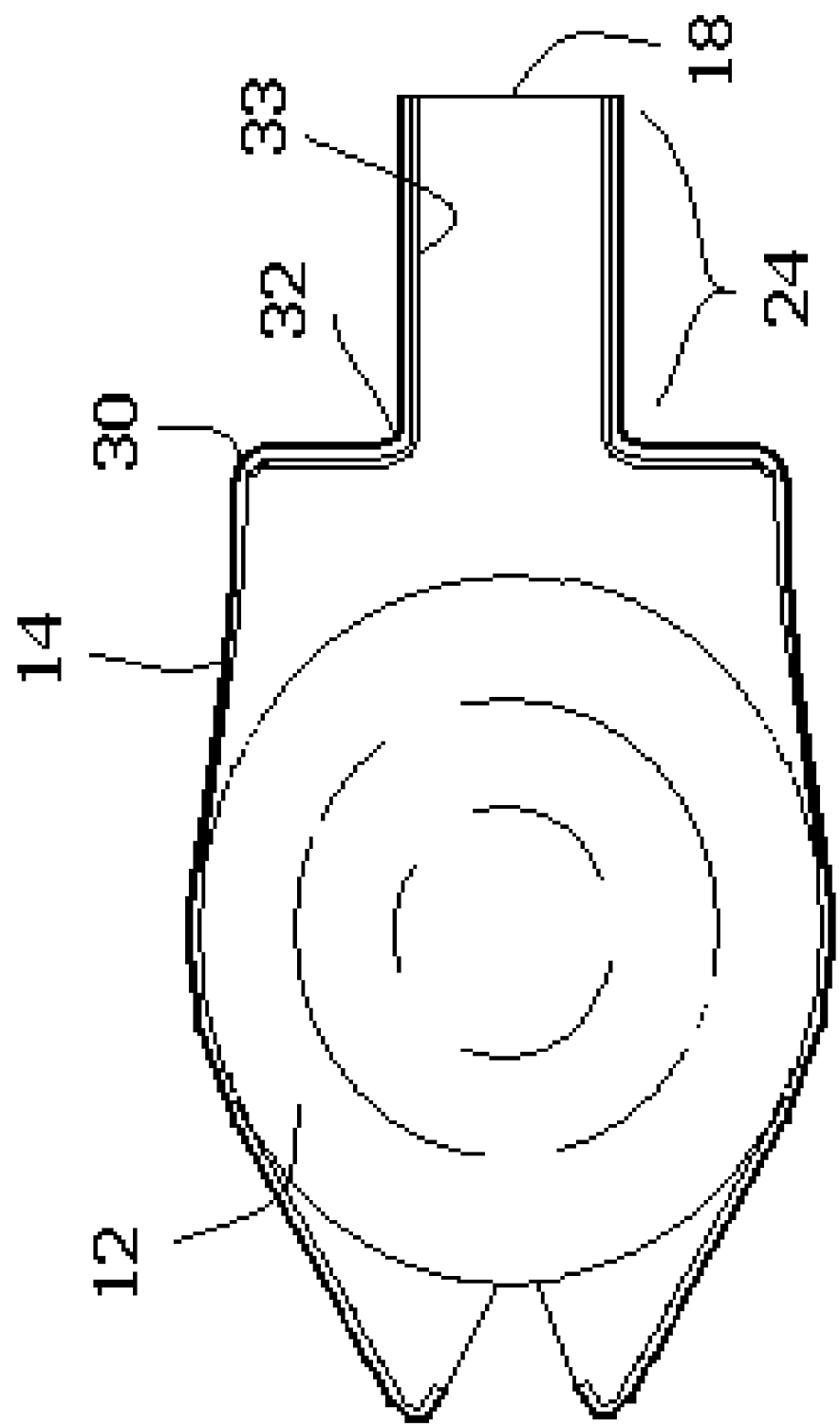
FIG. 2 shows the implant initially set into the compression sleeve.

Referring to FIG. 1 in conjunction with FIG. 2, it can be seen that the open second end 18 of the compression sleeve 14 contains an optional reinforced ring 26. If a reinforced ring 26 is used, it reinforces the open second end 18 and prevents the open second end 18 from tearing or non-elastically stretching as the pliable prosthetic implant 12 is forced through the open second end 18. If the open second end 18 is round, the open second end 18 has a diameter that is slightly smaller than the incision made by the surgeon and is designed to minimize the risk of substantial deformation of the pliable prosthetic implant 12. As such, if the pliable prosthetic implant 12 is a breast implant, the diameter is typically between three centimeters and seven centimeters. Likewise, if the open second end 18 is oblong in shape, the long axis of the oblong shape would typically be between three centimeters and seven centimeters.

The last stage 24 of the compression sleeve 14 that leads to the open second end 18 has the same internal shape and dimensions as does the open second end 18. As such, the diameter or long axis dimensions remain constant through the last stage 24 of the compression sleeve 14. The running length of the last stage 24 is between 30 millimeters and 100 millimeters, with a preferred length of about 50 millimeters. The length of the last stage 24 of the compression sleeve 14 must be at least as long as ten percent of the diameter of the pliable prosthetic implant 12 for reasons that are later detailed.

The first stage 22 of the compression sleeve 14 has a diameter or oblong axis that is at least twice as long as the diameter or oblong axis of the last stage 24. As such, the diameter or oblong axis of the first stage 22 can range between six centimeters and fourteen centimeters for a breast implant. The size of the compression sleeve 14 is appropriately selected for the size of the pliable prosthetic implant 12 being implanted. The running length of the first stage 22 can be any length that is capable of receiving and retaining the pliable prosthetic implant 12. The preferred range is between 20 centimeters and 40 centimeters.

The transition between the first stage 22 of the compression sleeve 14 and the last stage 24 of the compression sleeve 14 is abrupt. The compression sleeve 14 transitions from a horizontal orientation in the illustrated first stage 22 to a vertical orientation in a transition zone 28. In the transition zone 28, there are two opposing 90 degree curves 30, 32 that create an abrupt S-turn. Both the first curve 30 and the second curve 32 have a radius of curvature of between 10 millimeters and 30 millimeters. Referring to the orientation of the illustrated view, the compression sleeve 14 transitions from the horizontal orientation of the first stage 22 to a vertical orientation at the first curve 30. At the second curve 32, the compression sleeve 14 transitions from the vertical orientation of the transition zone 28 to the horizontal orientation of the last stage 24.

The interior of the compression sleeve 14 has a lubricant coating 33 that coats all stages 22, 24 and the transition zone 28. The coating preferably consists of an ionic lubricant as discussed by Mladick. These include any number of hydrophilic lubricants as manufactured by, or similar to, those manufactured by Advanced Biomaterials, AST Products, Biocoat, Coatingstogo, DSM, Harland MedicalSystems, Surface Solutions Group or PolyBioMed. Other conventional commercially available surgical lubricants can also be used, such as Surgilube® or gels (i.e., Aquasonic®) that may or may not contain common antibiotics such as bacitracin or other antimicrobial (antibacterial, antiviral, antifungal) agents.

Figure 3:
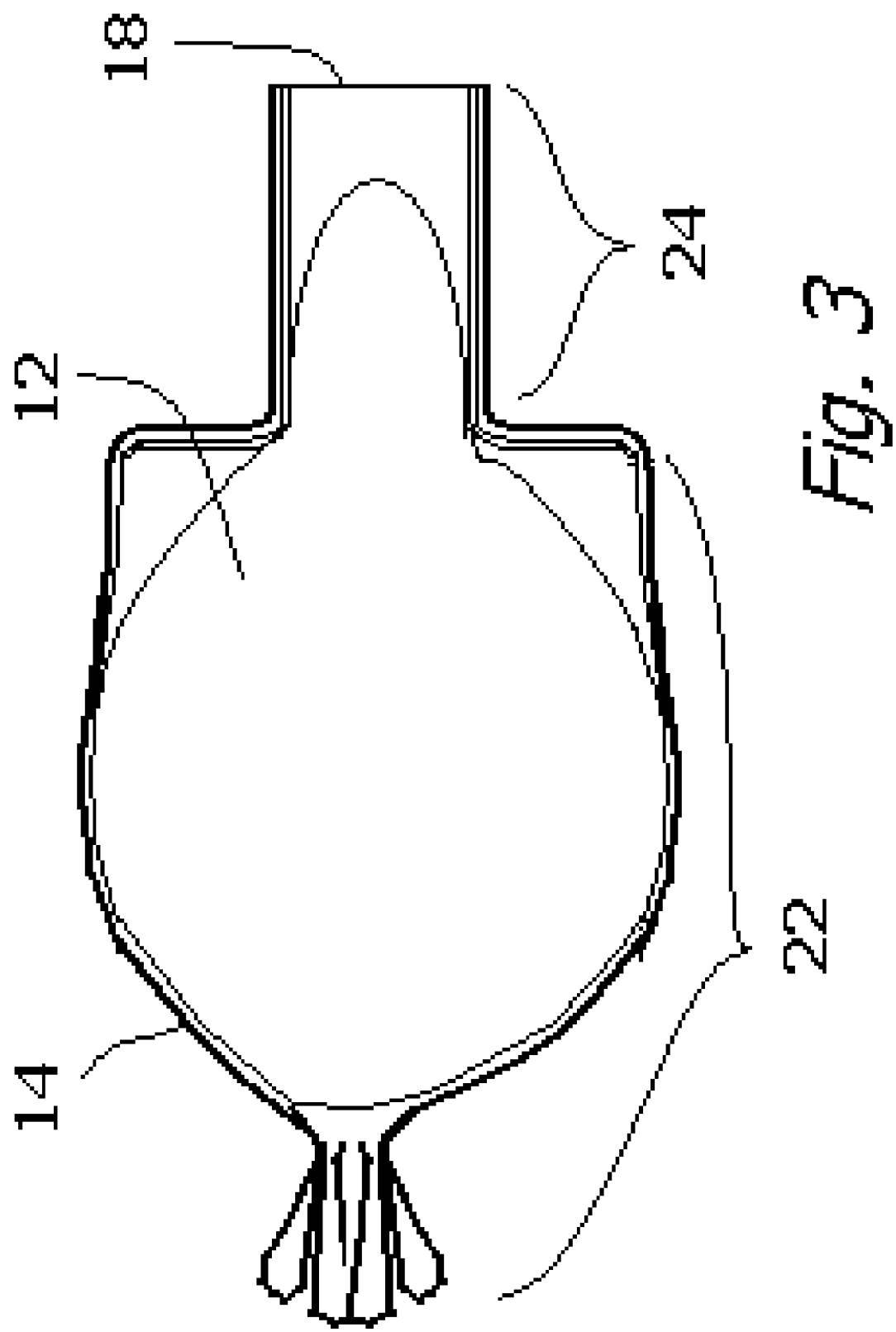
FIG. 3 shows the implant in the compression sleeve and being compressed and elongated by the compression sleeve.

Referring to FIG. 3 in conjunction with FIG. 1 and FIG. 2, it can be seen that the pliable prosthetic implant 12 is advanced into the first open end 16 of the compression sleeve 14 by manual manipulation. Once inside the compression sleeve 14, the first open end 16 of the compression sleeve 14 is manually closed. The compression sleeve 14 must stretch into tension in order to receive the pliable prosthetic implant 12. Once inside the compression sleeve 14, the tension of the compression sleeve 14 causes the pliable prosthetic implant 12 to elongate as it attempts to conform to the internal dimensions of the first stage 22.

The pliable prosthetic implant 12 is forced toward the second open end 18 of the compression sleeve 14 by applying forces to the exterior of the compression sleeve 14. These forces can be applied by the hands of the physician. Alternatively, the forces needed to advance the pliable prosthetic implant 12 can be applied by an external tool, such as a manual ringer.

Figure 4:
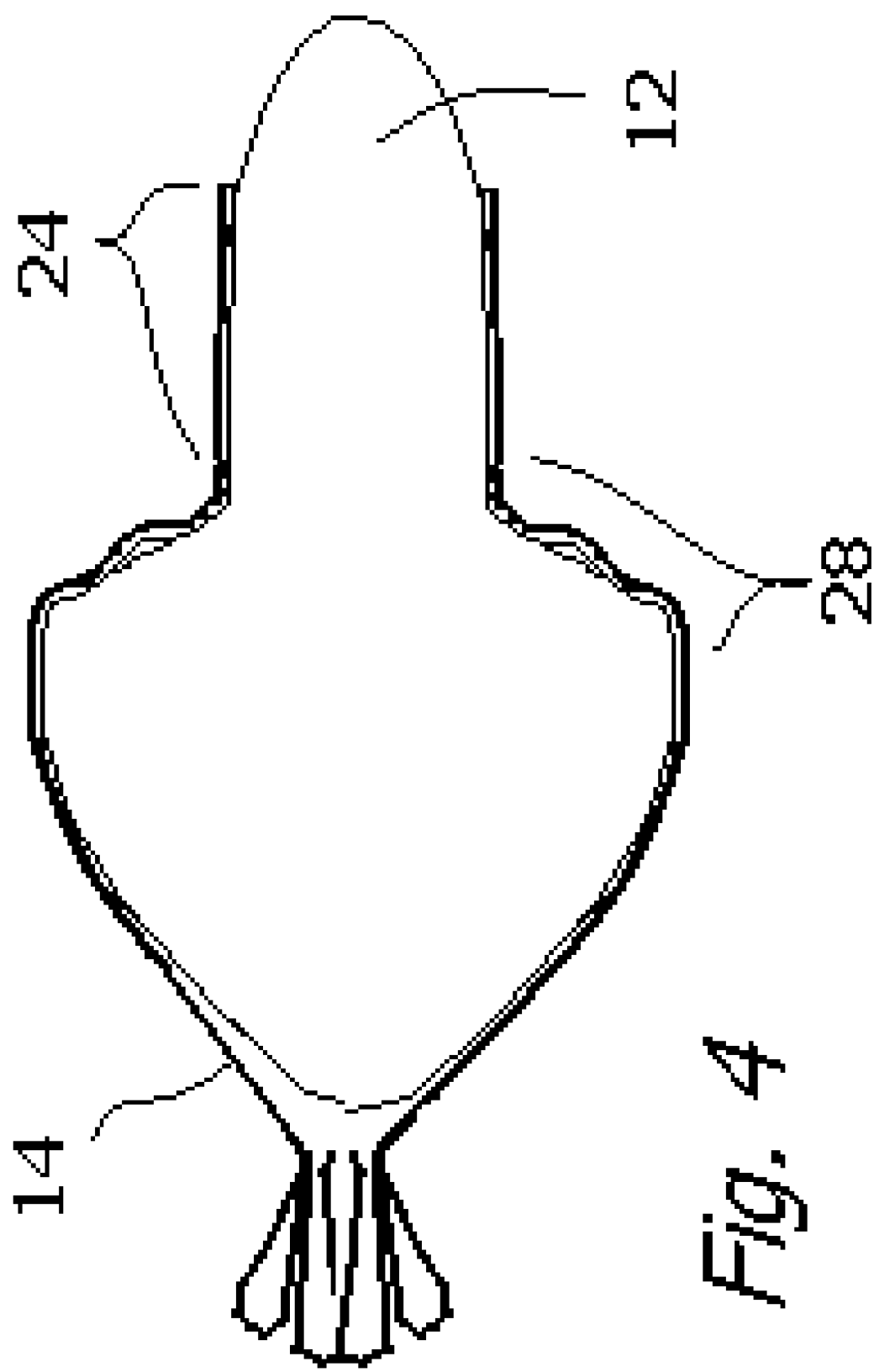
FIG. 4 shows the implant being displaced through the output end of the compression sleeve.

Referring now to FIGS. 3 and 4 in conjunction with FIG. 2, it will be understood that as the compression sleeve 14 is squeezed, the pliable prosthetic implant 12 is displaced toward the open second end 18 of the compression sleeve 14. As the pliable prosthetic implant 12 is compressed, the pliable prosthetic implant 12 becomes elongated and conforms more and more to the confines of the compression sleeve 14. The first stage 22 elongates and compresses the pliable prosthetic implant 12 to some initial degree. This conditions and elongates the pliable prosthetic implant 12 so that it can be displaced into the subsequent stage. Furthermore, the compression in the first stage 22 of the compression sleeve 14 properly orients and aligns the pliable prosthetic implant 12 to pass into the subsequent stage of the compression sleeve 14. Also the decreasing diameter of the portions of the compression sleeve 14 creates a controlled Bernoulli effect based on the difference in the diameters of the sleeve system which accelerates the implant through the device in a controlled manner.

As the length of the compression sleeve 14 is effectively shortened by being manually squeezed, the tension in the material of the compression sleeve 14 increases. Eventually, the tension builds to a point where the pliable prosthetic implant 12 is compressed enough to pass into the last stage 24. Once the pliable prosthetic implant 12 passes into the last stage 24, the tension needed to further advance the pliable prosthetic implant 12 decreases significantly. As such, a surgeon can decrease the pressures being applied to the compression sleeve 14 and can now control the movement of the pliable prosthetic implant 12 with more precision. Furthermore, the implant can now remain in this state as it is essentially "parked" in this position without the need for constant and ongoing pressure. The largest force that must be applied by a surgeon to the compression sleeve 14 is the force needed to move the pliable prosthetic implant 12 through the transition zone 28 from the first stage 22 and into the last stage 24. If a surgeon applies a very hard squeeze, the pliable prosthetic implant 12 may suddenly move from the first stage 22 into the last stage 24 through the transition zone 28. However, the pliable prosthetic implant 12 remains within the last stage 24 of the compression sleeve 14 and under the control of the surgeon. It has been found that if the running length of the last stage 24 is at least as long as ten percent of the diameter of the pliable prosthetic implant 12, then the friction prevents the pliable prosthetic implant 12 from shooting out in an uncontrolled manner. Rather, once the pliable prosthetic implant 12 is compressed into a size that can pass through the last stage 24, then the surgeon can reduce the compression forces while still advancing the pliable prosthetic implant 12 through the last stage 24 and out the open second end 18. It takes no greater force to move the pliable prosthetic implant 12 through the open second end 16 than it does to move the pliable prosthetic implant 12 through the last stage 24. As such, the pliable prosthetic implant 12 does not suddenly exit the compression sleeve 14 like a champagne cork. This control enables a surgeon to better position the pliable prosthetic implant 12 as it moves through an incision and into the patient. The controlled movement of the pliable prosthetic implant 12 further causes less bruising to the tissue of the body under the incision. This results in less swelling and a shorter recovery period from the surgery. In addition the decreased pressure and velocity and increased control reduces rotation of the implant during introduction to the pocket a critical distinction for anatomically shaped implants and allows visualization for proper orientation on the initial effort.

The controlled ejection of the pliable prosthetic implant 12 by the present invention differs significantly from prior art funnels that shoot a breast implant into an incision in a sudden and uncontrolled, unmonitored and poorly visualized manner. The sudden ejection of an implant by prior art systems, causes unnecessary trauma and often requires that a surgeon enter the incision with auxiliary instrumentation or digital manipulation to better position the implant. This causes more bruising, more swelling and can cause damage to the prosthetic as well as possible contamination from transmission of skin bacteria to the implant pocket.

Figure 5:
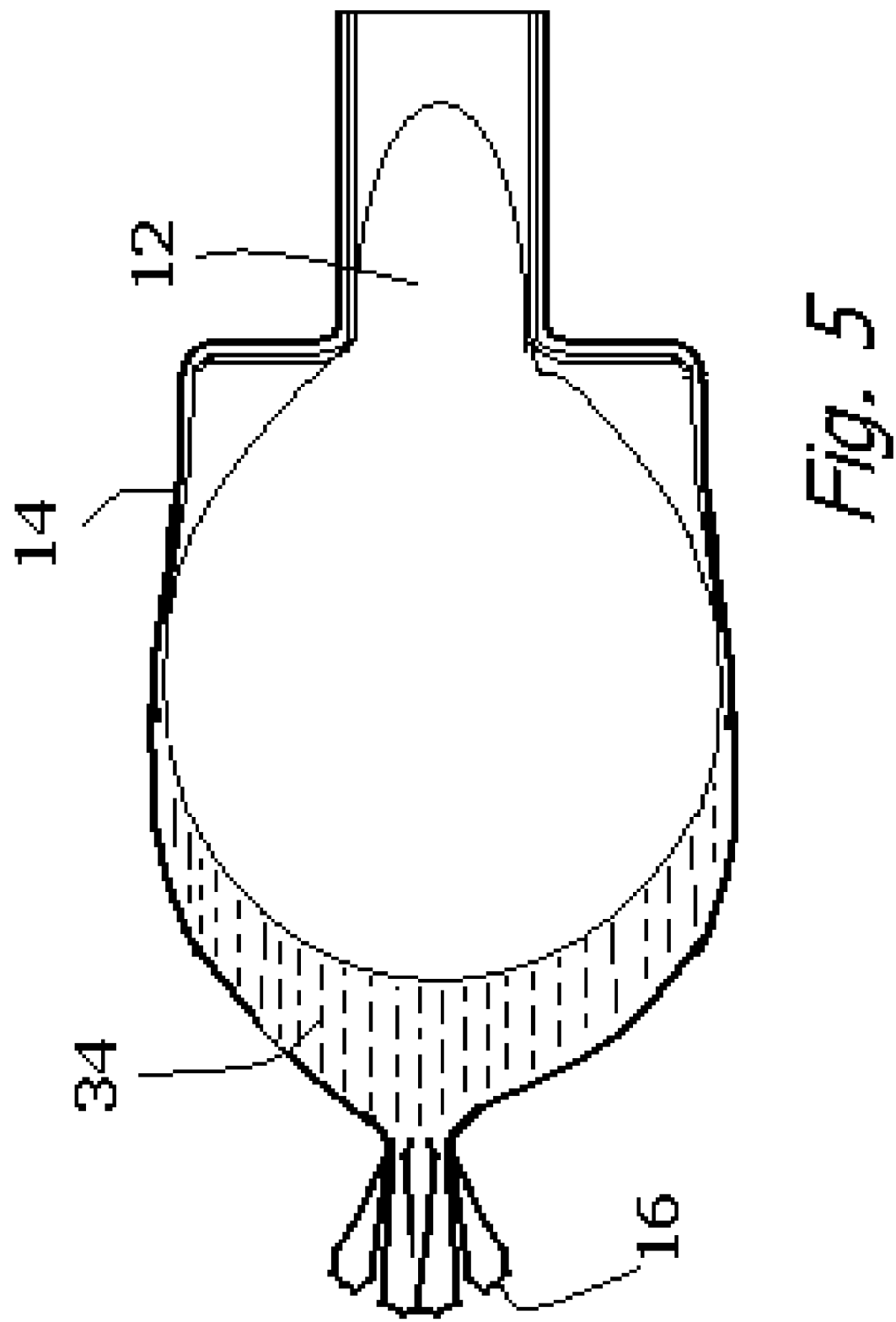
FIG. 5 shows the compression sleeve being supplemented with a volume of an antimicrobial solution.

Referring to FIG. 5, a slight variation in the ejection procedure is shown. In this embodiment, a volume of an antimicrobial solution 34 is entered into the compression sleeve 14 after the pliable prosthetic implant 12 is inserted. The open first end 16 of the compression sleeve 14 is then closed. This traps the antimicrobial solution 34 within the compression sleeve 14 on one side of the pliable prosthetic implant 12. As the compression sleeve 14 is compressed, the antimicrobial solution 34 applies hydraulic forces to the pliable prosthetic implant 12. This produces a few beneficial side effects. First, the hydraulic forces act to expand the compression sleeve 14 around the pliable prosthetic implant 12. This enables the antimicrobial solution 34 to pass between the material of the compression sleeve 14 and the pliable prosthetic implant 12. This lubricates the interface and makes the pliable prosthetic breast implant 12 easier to move. Second, the hydraulic pressure counteracts buckles and folds in the compression sleeve 14 that occur when the compression sleeve 14 is being compressed. This inhibits folds and buckles from pinching the pliable prosthetic implant 12 and inhibiting its forward movement. The antimicrobial solution 34 also helps maintain the pliable prosthetic implant 12 in a sterile condition as it passes through the compression sleeve 14. Lastly, the hydraulic forces act evenly upon the pliable prosthetic implant 12. The pliable prosthetic implant 12 is therefore moved forward without twisting or rotating as it contacts the passing interior of the compression sleeve 14.

Referring to FIG. 6, another modification to the invention is shown. In the embodiment of FIG. 6, reinforcement ribs 40 are formed along the length of the compression sleeve 14b. The reinforcement ribs 40 lay in parallel planes that are parallel to the open first end 16 and the open second end 18. The reinforcement ribs 40 make the compression sleeve 14b harder to deform in the areas that contain the reinforcement ribs 40. The reinforcement ribs 40 may be rings that encircle the compression sleeve 14b. Alternatively, the reinforcement ribs 40 may only partially encircle the compression sleeve 14b like the ribs of a snake.

The reinforcement ribs 40 make it easier for a surgeon to compress the compression sleeve 14b once an implant 12 has been inserted into the compression sleeve 14b. The reinforcement ribs 40 also help propel the pliable prosthetic implant 12 forward as it is advanced over the implant 12 and contracts behind the implant 12.

It will be understood that the embodiments of the present invention that are illustrated and described are merely exemplary and that a person skilled in the art can make many variations to those embodiments. All such embodiments are intended to be included within the scope of the present invention as defined by the appended claims.

What is claimed is:

1. A system for advancing a pliable prosthetic into a surgical incision, comprising:
    a compression sleeve having a first open end, a second open end, a first stage of a first length, and a second stage of a second length, wherein said first stage has a first cross-sectional profile that evenly extends along said first length, said second stage has a second cross-sectional profile that extends along said second length, and wherein said first stage is accessible through said open first end and said second stage is accessible through said open second end;
    a transition zone disposed between said first stage and said second stage, wherein said transition zone has a length of less than 40 centimeters;
    wherein said sleeve is comprised of a flexible material and wherein said first cross-sectional profile of said first stage is larger than said second cross-sectional profile of said second stage.

2. The system according to claim 1, wherein said flexible material is transparent, wherein an orientation for said pliable prosthetic can be observed through said flexible material.

3. The system according to claim 1, further including a lubricant coating applied to said first stage and said second stage within said compression sleeve.

4. The system according to claim 3, wherein said lubricant includes an antimicrobial.

5. The system according to claim 1, wherein said first length is at least 100 millimeters long.

6. The system according to claim 1, further including slots formed in said first section of said compression sleeve proximate said first open end.

7. The system according to claim 1, wherein said second end has a maximum opening size of between three centimeters and seven centimeters.

8. The system according to claim 1, further including a volume of fluid within said compression sleeve.

9. A system for advancing a pliable prosthetic into a surgical incision, comprising:
    a compression sleeve having a first open end, a second open end, a first stage of a first length of at least 100 millimeters, and a second stage of a second length, wherein said first stage has a first cross-sectional profile that evenly extends along said first length, said second stage has a second cross-sectional profile that extends along said second length, and wherein said first stage is accessible through said open first end and said second stage is accessible through said open second end;
    wherein said sleeve is comprised of a flexible material and wherein said first cross-sectional profile of said first stage is larger than said second cross-sectional profile of said second stage.

10. The system according to claim 9, wherein said second length is at least 30 millimeters long.

11. The system according to claim 9, wherein said flexible material is transparent, wherein an orientation for said pliable prosthetic can be observed through said flexible material.

12. The system according to claim 9, further including a lubricant coating applied to said first stage and said second stage within said compression sleeve.

13. The system according to claim 9, wherein a transition zone is disposed between said first stage and said second stage.

14. The system according to claim 13, wherein said transition zone has a length of less than 40 centimeters.

15. The system according to claim 9, further including slots formed in said first section of said compression sleeve proximate said first open end.

16. The system according to claim 9, wherein said second end has a maximum opening size of between three centimeters and seven centimeters.

* * * * *